(12) United States Patent
Schober et al.

(10) Patent No.: US 12,146,129 B2
(45) Date of Patent: Nov. 19, 2024

(54) MICROBIOREACTOR ASSEMBLY

(71) Applicant: TECHNISCHE UNIVERSITAET ILMENAU, Ilmenau (DE)

(72) Inventors: Andreas Schober, Erfurt (DE); Frank Weise, Ilmenau (DE); Joerg Hampl, Erfurt (DE); Gregor Schlingloff, Ilmenau (DE)

(73) Assignee: TECHNISCHE UNIVERSITAET ILMENAU, Ilmenau (DE)

( * ) Notice: Subject to any disclaimer, the term of this patent is extended or adjusted under 35 U.S.C. 154(b) by 689 days.

(21) Appl. No.: 16/772,946

(22) PCT Filed: Dec. 15, 2017

(86) PCT No.: PCT/EP2017/083150
§ 371 (c)(1),
(2) Date: Jun. 15, 2020

(87) PCT Pub. No.: WO2019/114996
PCT Pub. Date: Jun. 20, 2019

(65) Prior Publication Data
US 2021/0155886 A1 May 27, 2021

(51) Int. Cl.
*C12M 1/12* (2006.01)
*C12M 1/00* (2006.01)
*C12M 1/32* (2006.01)

(52) U.S. Cl.
CPC ............ *C12M 25/04* (2013.01); *C12M 23/12* (2013.01); *C12M 23/22* (2013.01); *C12M 23/38* (2013.01);
(Continued)

(58) Field of Classification Search
CPC ...... C12M 25/04; C12M 25/14; C12M 23/12; C12M 23/22; C12M 23/38; C12M 23/40; C12M 37/04
(Continued)

(56) References Cited

U.S. PATENT DOCUMENTS 5,801,055 A * 9/1998 Henderson .......... B01L 3/50255
  435/297.5
8,865,464 B2 * 10/2014 Takayama ............ C12N 5/0075
  435/325

(Continued)

FOREIGN PATENT DOCUMENTS

DE 19806681 A1 8/1999
DE 10118905 A1 10/2002
(Continued)

*Primary Examiner* — Michael L Hobbs
*Assistant Examiner* — Lenora A Abel
(74) *Attorney, Agent, or Firm* — Stuart H. Mayer; Kaplan Breyer Schwarz LLP

(57) ABSTRACT

The invention relates to a microbioreactor assembly (01) having a plurality of microbioreactors. The microbioreactor assembly comprises a microtiter plate (02) having numerous wells (09) in a predefined grid arrangement, a closed bottom surface (14) and an open upper face. An insert unit (03) is also provided, which is arranged on the upper face of the microtiter plate (02) and has numerous inserts (11) in the same grid arrangement, each insert (11) engaging in a well (09), and the well (09) being divided into at least two regions (12, 17). Finally, the microbioreactor assembly comprises an activation unit (04), which is placed on the insert unit (03) and has numerous pumps (26), each of which is connected to supply channels (19), which allow the transport of fluid between the two regions (12, 17).

8 Claims, 2 Drawing Sheets

(52) U.S. Cl.
CPC ............ *C12M 23/40* (2013.01); *C12M 25/14* (2013.01); *C12M 37/04* (2013.01)

(58) Field of Classification Search
USPC ...................................................... 435/305.3
See application file for complete search history.

(56) References Cited

U.S. PATENT DOCUMENTS

| | | | |
|---|---|---|---|
| 2003/0186217 | A1* | 10/2003 | Bader .................... C12M 23/24 435/287.1 |
| 2010/0029000 | A1 | 2/2010 | Zhong |
| 2013/0177916 | A1 | 7/2013 | Chen |
| 2015/0247112 | A1 | 9/2015 | Orr |

FOREIGN PATENT DOCUMENTS

| | | |
|---|---|---|
| DE | 69831115 T2 | 6/2006 |
| DE | 202006017853 U1 | 1/2007 |
| DE | 102010037968 A1 | 4/2012 |
| EP | 0866119 A2 | 9/1998 |
| EP | 0866120 A2 | 9/1998 |
| EP | 1160573 A2 | 12/2001 |
| EP | 2690167 A1 | 1/2014 |
| EP | 3190172 A2 | 7/2017 |
| JP | 2006039171 A | 2/2006 |
| WO | 02/24861 A2 | 3/2002 |
| WO | 2011/035938 A1 | 3/2011 |
| WO | 2011035937 A1 | 3/2011 |
| WO | 2013/082612 A1 | 6/2013 |

\* cited by examiner

MICROBIOREACTOR ASSEMBLY

BACKGROUND OF THE INVENTION

The invention relates to a microbioreactor assembly comprising a plurality of microbioreactors. The arrangement comprises a microtiter plate having numerous wells in a predetermined grid arrangement.

The construction of microtiter plates (microwell plates) is known in principle and is used for the examination of biological substances, for example absorption measurement in photometers or screening examinations of numerous modifications to a basic substance. Microtiter plates usually have a rectangular basic shape and consist of plastics material or glass. A microtiter plate has numerous wells that are isolated from one another, which are arranged in a predetermined grid. The exact dimensions are usually selected according to an ANSI standard. The wells are available in different shapes, for example with a flat base or a U-shaped tapered base in each well. In any case, the base surface of the microtiter plate is closed and the top is open such that the cavity of each well is accessible from the top.

DE 198 06 681 A1 discloses a microtiter plate comprising a base plate which is transparent to light and a cavity plate which is open on two opposite surfaces and has a matrix-like arrangement of the cavities or wells. Base plates and cavity plates are interconnected in a non-detachable and liquid-tight manner. The base plate has a flat, structureless surface and, on its first surface facing the wells, carries a layer system consisting of at least two layers each having a different refractive index.

DE 20 2006 017 853 U1 describes an insert for a microtiter plate, consisting of a carrier structure in which at least one depression is made, the upper diameter of the depression being selected such that it can be inserted into a depression in the microtiter plate. The bottom of each depression has at least one microcavity that is shaped downwards. The insert is provided with pores at least in part.

In addition to microtiter plates, there are other approaches for providing cavities for the examination of biological substances.

For example, WO 2011/035937 A1 describes a microstructured molded body comprising a film which is divided into undeformed regions and thinned stretching regions. Microstructures are formed at least in some of the thinned stretching regions, pores being formed in at least one of the thinned stretching regions and at least some of the undeformed regions being impermeable.

Furthermore, WO 2011/035938 A1 discloses a microstructured molded body which has a film-like main body which comprises a first film layer and a second film layer located underneath, the second film layer having recesses having a diameter of less than 2 mm, which are formed by deformed regions of the first film layer, by means of which cavities are formed. At least some of the deformed regions of the first film layer have pores. The regions of the film-like base body are impermeable outside the recesses.

DE 10 2010 037 968 A1 describes a structure for simulating a sinusoid, which can be inserted into a microtiter plate. The structure comprises a plurality of layers of a porous material arranged one above the other, a space being formed between each of the layers. The spaces are connected by channels formed in the layers for conveying a fluid.

Until now, no assemblies have been disclosed in the prior art which allow for the cultivation of biological substances in a large number of variations and at the same time allow for the examination of the substances, in particular using conventional optical observation apparatuses, and moreover can be implemented in a cost-effective manner using widely available systems.

Taking into account these requirements, the problem addressed by the present invention is to provide a microbioreactor system based on microtiter plates which allows for a parallel supply of a plurality of microbioreactors which are formed in the individual wells. At the same time, it is intended to be possible to observe the cultivated biological substances in all microbioreactors, preferably using known inverse microscopes. Lastly, the aim is to make the microbioreactor assembly simple and cost-effective to produce.

SUMMARY OF THE INVENTION

The problem is solved by a microbioreactor assembly according to the appended claim 1.

The microbioreactor assembly according to the invention implements a large number of microbioreactors and, for this purpose, comprises a microtiter plate having numerous wells in a predetermined, preferably standardized, grid arrangement. In a manner known per se, the microtiter plate has a closed base surface, which preferably allows for visual observation, i.e. lets light beams pass therethrough. The individual wells are open at the top of the microtiter plate, such that inserts from an insert unit which is arranged on the top of the microtiter plate can be inserted from there. The numerous inserts have the same grid arrangement, such that each insert engages in a well. The insert divides the well into at least two regions, in particular a cell-cultivation region and a closed region for the transport of nutrients.

An activation unit is also part of the microbioreactor assembly. The activation unit is placed on the insert unit and has numerous pumps which are connected to the regions formed by the inserts, namely by supply channels which enable fluid or nutrient transport between the two regions.

One advantage of the invention can be considered to be that the individual cell-cultivation regions can be observed through the underside of the microtiter plate and, at the same time, can also be used in automatic pipetting systems and in standard analysis devices (e.g. fluorescence microplate readers) through the upper opening. It is therefore fully compatible with standardized microtiter plates, including all handling and analysis options.

According to a preferred embodiment, each of the inserts of the insert unit has a microstructured molded body which is arranged in parallel with the base surface of the microtiter plate and provides an adhesion scaffold for cell cultures. For example, the molded body can be formed according to the above-mentioned WO 2011/035938 A1.

A modified embodiment is characterized in that at least one insert, preferably a plurality of inserts, has at least two microstructured molded bodies which are positioned in parallel with one another and so as to be axially spaced apart from one another.

It is advantageous for the base surface to be visually transparent, at least in the region of the molded bodies, and not to be covered by frame elements or the like. This allows for the visual observation of the substances or cell cultures on the molded bodies through the base surface, for which purpose standard inverted microscopes can preferably be used. The microbioreactor assembly according to the invention can therefore be clamped into existing observation assemblies such as a conventional microtiter plate in order to carry out the observations.

According to a preferred embodiment, a distributor channel system is formed in the activation unit, via which the plurality of pumps is supplied with compressed air in order to carry out the pumping operation. In a simple case, all the pumps are driven in parallel, such that the same flow conditions prevail in each well. In particular, the pumps transport a nutrient solution for supplying the cell cultures that are located on the molded bodies of the inserts. In alternative configurations, the pumps can also be driven individually or in groups, for which purpose targeted actuation is made possible, for example by switching valves, which may be an integral part of the activation unit.

An advantageous embodiment is characterized in that the insert unit comprises a sealing structure. This is designed such that, on each of the inserts, a pressure-open region, into which cell cultures can be introduced, is separated from a closed region, in which nutrient solution can be circulated. The open region for the cell cultures is preferably cylindrical in shape and is positioned coaxially in the associated well. The covering unit is preferably provided with a central opening above the open regions, through which substances can be added using a pipette. The closed region may also be arranged cylindrically and coaxially or may be inserted into the open region in the form of tubes or capillaries. The two regions are preferably molded onto the sealing structure, inserted therein, or formed in one piece with the sealing structure. The sealing structure extends substantially in the plane of the microtiter plate and lies flat thereon.

It is also advantageous for the insert unit to comprise a supply channel system which is coupled to each of its inserts in order to make it possible to supply and discharge a nutrient solution to and from the inserts. For this purpose, the insert unit may be composed of a plurality of partial layers in order to form the required cavities.

According to a modified embodiment, the microbioreactor assembly further comprises a cover plate which is attached to the activation unit to close the microbioreactor assembly at the top. In this case, the cover plate can be removed if necessary, for example to make the central openings into the inserts accessible.

BRIEF DESCRIPTION OF THE DRAWINGS

Further details and advantages emerge from the following description of preferred embodiments of the microbioreactor assembly according to the invention, with reference to the drawings, in which.

DETAILED DESCRIPTION OF THE INVENTION

Figure 1:
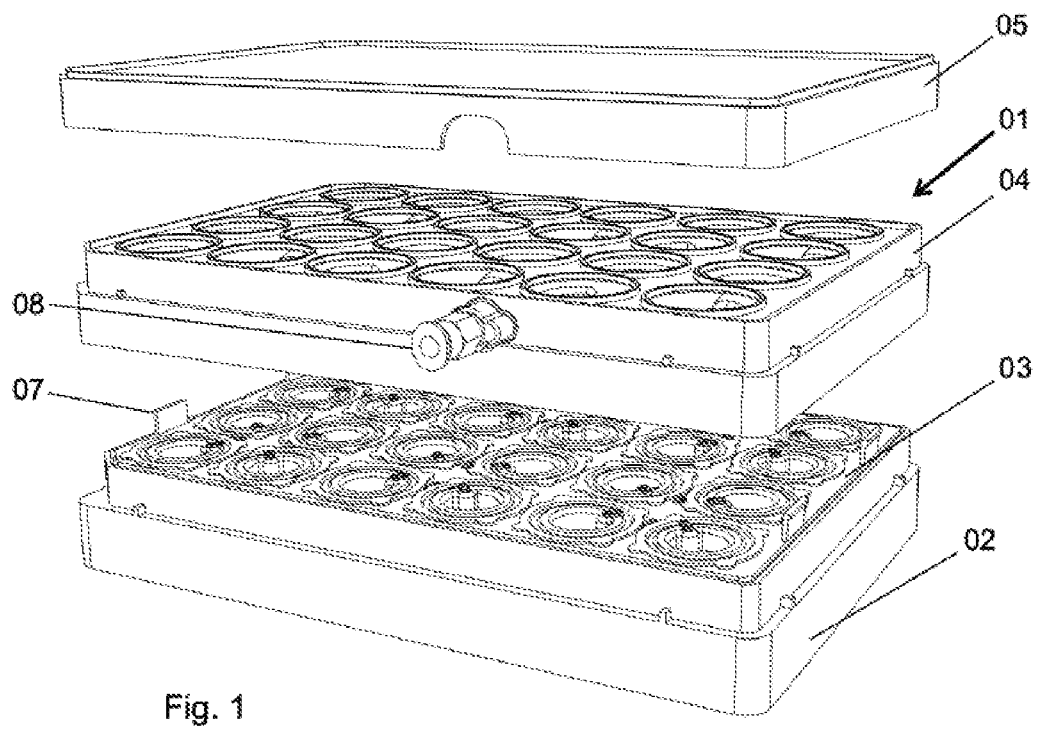
FIG. 1 is an exploded perspective view of a first embodiment of a microbioreactor assembly according to the invention.

FIG. 1 is an exploded perspective view of a microbioreactor assembly 01 according to the invention. The microbioreactor assembly 01 has a plurality of main groups, namely a microtiter plate 02, an insert unit 03 placed on the top thereof, and an activation unit 04 arranged above the insert unit. In the embodiment shown, there is also a separate cover plate 05 which covers the activation unit on the top. The main groups are layered one on top of the other such that the microtiter plate 02 acts as the lower support. The main groups are securely interconnected after assembly, for example by locking elements 07, but can be detached if necessary. A supply connection 08 is provided on the activation unit 04, by means of which, for example, compressed air and a nutrient solution can be supplied. Additional connections (not shown) can be provided on the insert unit if necessary.

Figure 2:
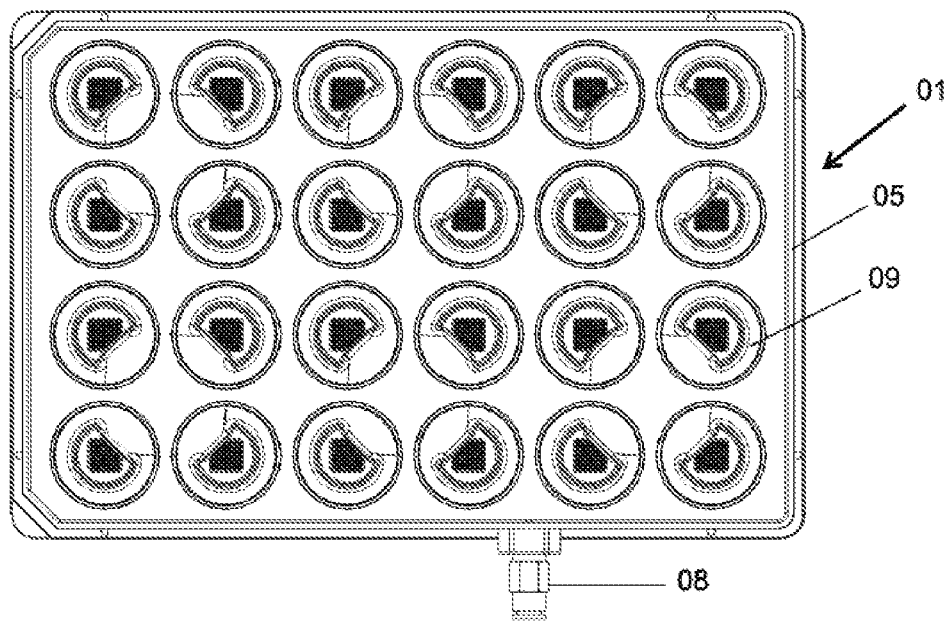
FIG. 2 is a plan view of the assembled microbioreactor assembly.

FIG. 2 is a plan view of the microbioreactor assembly 01, the cover plate 05 being made of transparent material such that the individual wells 09 of the microtiter plate 02 therebelow can be seen. In the example shown, the wells 09 are arranged in a 6×4 matrix. Of course, other microtiter plates can also be used, the other main groups then having to be adapted accordingly.

Figure 3:
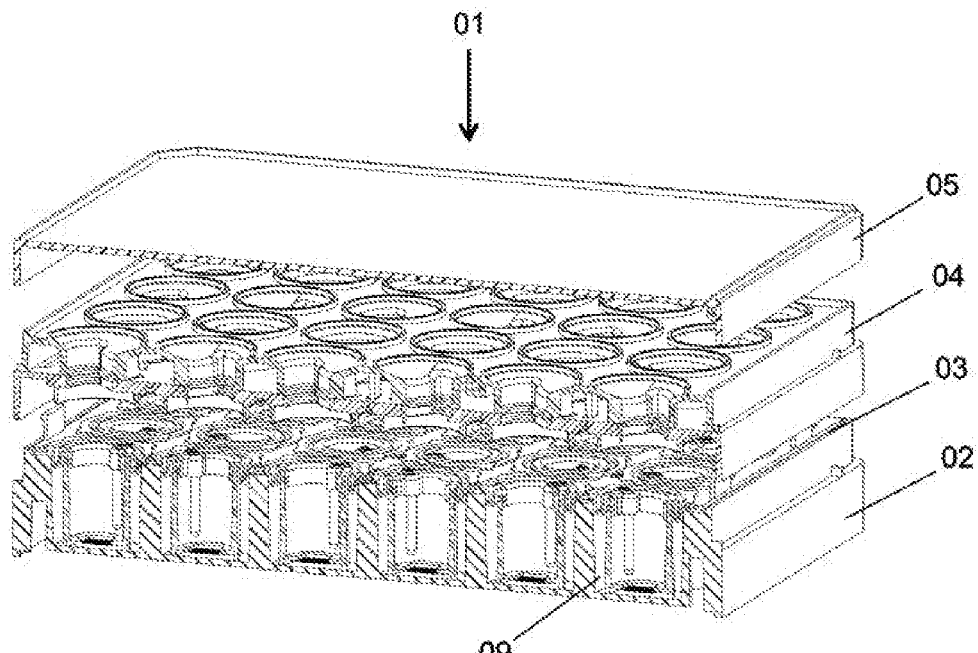
FIG. 3 is a sectional view of the microbioreactor assembly before being assembled.

FIG. 3 is again a sectional exploded view of the microbioreactor assembly 01. It can be clearly seen here that the main groups are stacked on top of one another in an aligned manner and the matrix arrangement of the microtiter plate 02 is repeated in the layers above. In this way, numerous microbioreactors are formed, all of which are identical in structure but can be populated with different cell cultures.

Figure 4:
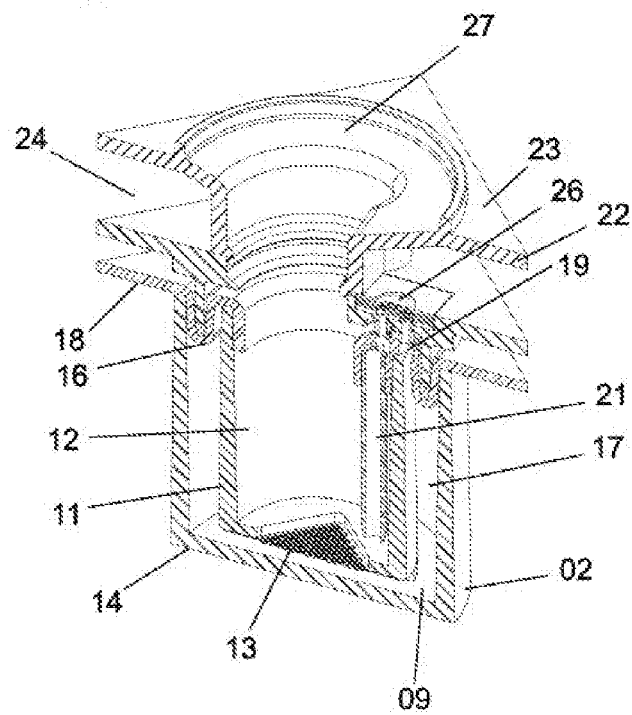
FIG. 4 is a sectional perspective view of a detail of a single well comprising an insert.

FIG. 4 is a perspective sectional view of such a microbioreactor, which is composed of sections of the above-mentioned main groups, as follows: An insert 11, which is part of the insert unit 03, engages in the blind hole-like well 09 of the microtiter plate 02. The insert 11 has a cylindrical cell-cultivation region 12, in which biological substances can be introduced and cultivated. At the bottom of the cell-cultivation region 12 there is a microstructured molded body 13 on which cell cultures can be populated. A base surface 14 of the microtiter plate 02 is transparent, at least below the microstructured molded body 13, in order to allow for visual observation of the populated cell cultures. In the upper region, the wall of the insert 11 opens into a sealing structure 16, which seals the open cell-cultivation region 12 against a closed region 17. In the embodiment shown, the closed region 17 extends coaxially between the inner wall of the well 09 and the outer wall of the insert 11. The insert unit 03 also includes a supporting frame 18, which stabilizes the sealing structure 16 and also provides a supply channel 19 through which nutrient solution can be transported. A suction capillary 21 is connected to the supply channel 19 and extends axially in the cell-cultivation region 12. Nutrient solution can thus be circulated between the cell-cultivation region 12 and the closed region 17 via the supply channel 19.

The activation unit 04 is placed on top of the insert unit 03, which, in the example shown, is composed of a lower plate 22 and an upper plate 23, between which a closed pressure chamber 24 is formed. In the lower plate 22, a membrane 26 is inserted, which acts on the supply channel system 19 and can be acted upon by compressed air from the pressure chamber 24. If pressure is built up between the lower plate 22 and the upper plate 23 by the supply of compressed air via the supply connection 08, the membrane 26 acts as a pump which drives the delivery of the nutrient solution in the closed region 17.

Finally, in the activation unit 04, a central opening 27 that is open at the top is provided, which opens into the cell-cultivation region 12. Substances can preferably be added through the central opening 27 using an automated pipette. The central opening 27 can be closed by the cover plate 05 if it is not necessary for anything to be added.

The invention claimed is:
1. Microbioreactor assembly comprising a plurality of microbioreactors, comprising:

a microtiter plate having numerous wells in a predetermined grid arrangement, a closed base surface, and an open top;

an insert unit, which is arranged on the top of the microtiter plate and has numerous inserts in the same grid arrangement, wherein one insert engages in each well, and wherein the well is divided at least into two regions;

wherein the insert unit comprises a sealing structure which, on each of the individual inserts, separates a pressure-open region, into which cell cultures can be introduced, from a closed region, in which nutrient solution can be circulated;

an activation unit, which is placed on the insert unit and has numerous pumps, each of which is connected to supply channels, which enable fluid transport between the two regions.

2. Microbioreactor assembly according to claim 1, wherein the inserts of the insert unit each have a microstructured molded body which is arranged in parallel with the base surface of the microtiter plate and provides an adhesion scaffold for cell cultures.

3. Microbioreactor assembly according to claim 2, wherein at least one insert, preferably a plurality of inserts, has at least two microstructured molded bodies which are positioned in parallel with one another and so as to be axially spaced apart, and each provide an adhesion scaffold for cell cultures.

4. Microbioreactor assembly according to claim 2, wherein the base surface is visually transparent at least in the region of the molded bodies in order to allow for visual observation through the base surface.

5. Microbioreactor assembly according to claim 1, wherein the activation unit comprises a distributor channel system, by means of which the pumps can be supplied with compressed air.

6. Microbioreactor assembly according to claim 1, wherein the insert unit comprises a supply channel system which communicates with each insert in order to make it possible to supply and discharge a nutrient solution.

7. Microbioreactor assembly according to claim 1, wherein the activation unit has a central opening above each insert, which opens into a cell-cultivation region and by means of which substances can be pipetted in.

8. Microbioreactor assembly according to claim 7, wherein it further comprises a cover plate, which is attached to the activation unit to close the central openings.

* * * * *